United States Patent [19]

Adams

[11] Patent Number: 5,776,143
[45] Date of Patent: Jul. 7, 1998

[54] STEREOSTATIC POINTING DEVICE

[75] Inventor: Laurence Pentecost Adams, Cape Town, South Africa

[73] Assignee: Implico B.V., Amsterdam, Netherlands

[21] Appl. No.: 693,115

[22] PCT Filed: Feb. 17, 1995

[86] PCT No.: PCT/NL95/00063

§ 371 Date: Nov. 15, 1996

§ 102(e) Date: Nov. 15, 1996

[87] PCT Pub. No.: WO95/22297

PCT Pub. Date: Aug. 24, 1995

[30] Foreign Application Priority Data

Feb. 18, 1994 [ZA] South Africa ............... 94/1132

[51] Int. Cl.⁶ .................................................. A61B 19/00
[52] U.S. Cl. .................................................. 606/130
[58] Field of Search ........................ 606/129, 130; 604/116; 269/328; 403/90, 115, 131

[56] References Cited

U.S. PATENT DOCUMENTS 3,457,922  7/1969  Ray .
4,809,694  3/1989  Ferrara ........................ 606/130
4,955,891  9/1990  Carol ........................... 606/130

Primary Examiner—Michael Powell Buiz
Assistant Examiner—William W. Lewis
Attorney, Agent, or Firm—Frommer Lawrence & Haug LLP; William S. Frommer

[57] ABSTRACT

A surgical guidance device for the precise positioning of a surgical object comprises a base having three feet which define a first plane and which are adapted for location on markers secured to a patient's body. The device includes a swivel head which is constrained for movement in a second plane, and a guide for the surgical object. The guide is mounted on the swivel head so that it can swivel with respect to the swivel head in all directions about a pivot point. The device also includes a locking member for locking the swivel head in a selected translational position in the second plane and the guide in a selected angular position with respect to the swivel head. The surgical guidance device forms part of a kit including three markers securable to a patient's body and on which the feet of the device are respectively locatable.

8 Claims, 3 Drawing Sheets

STEREOSTATIC POINTING DEVICE

The invention relates to a surgical guidance device according to the preamble of claim 1. It also relates to a method of guiding a surgical object to a target positioned in a patient.

The surgical guidance device according to the preamble of claim 1 is for example known from US-A-3,457,922 or US-A-3,073,310.

Both known devices have to be set up whilst attached to the patient's skull and X-rays are then taken of the patient while the device is so attached. Both devices have skill settings and protractor settings in order to be able to set up the device. In order to set the known devices up, the known devices have to be attached to the patient's skull.

According to the invention the surgical guidance device is characterized by the features of claim 1.

The swivel head may be mounted on a radius arm, the radius arm may be mounted on the base so as to be pivotally displaceable with respect to the base about a pivot axis normal to the first plane, and the radius arm may be slidably displaceable with respect to the base or the swivel head, whereby the radial distance between the swivel head and pivot axis can be varied.

The guide may comprise a guide tube along which a pin forming the surgical object or having the surgical object attached thereto, can slide with little clearance, the tube being connected to the swivel head via a ball-and-socket connection.

The guide tube may have a spherical formation between the ends and on the outside thereof, and the swivel head may comprise a pair of annular clamping plates between which the spherical formation is held, the clamping plates and the spherical formation forming said ball-and-socket connection, and locking of the guide in a selected angular position with respect to the swivel head being effected by clamping the clamping plates together to grip the spherical formation therebetween.

The surgical guidance device may have, in combination therewith as part of a kit, a phantom which comprises a plate having an opening therein and, spaced around the opening, three locating formations whose positions relative to one another correspond to the positions of said feet relative to one another, and the phantom further comprising a target block below the opening, the target block being slidable in three mutually orthogonal directions along graduated slides.

Further according to the invention there is provided a method of guiding a surgical object to a target position in a patient, the method comprising:

utilising a guidance device having a base with three feet which define a first plane, a swivel head which is constrained for movement in a second plane spaced from and parallel to the first plane, and a guide for the surgical object, the guide being mounted on the swivel head so that it can swivel with respect to the swivel head in all directions about a pivot point, applying at least three markers to the body of the patient, the positions of the markers relative to one another corresponding to the positions of said feet relative to one another;

determining the co-ordinates of the target position and each of the markers, in a three coordinate system;

setting up the guidance device by adjusting the translational position of the swivel head in the second plane and adjusting the angular position of the guide with respect to the swivel head;

locking the swivel head and the guide in their adjusted positions;

placing the guidance device on the patient so that the feet are in register with the positions of said markers; and inserting the surgical object into the patient along the guide.

The invention will now be described in more detail, by way of example, with reference to the accompanying drawings.

In the drawings:

FIG. 3 is a section on III—III in FIGS. 1 and 2;

FIG. 4 is a section on IV—IV in FIG. 2, drawn to a larger scale;

FIG. 7 is a side view, shown partly in section, of an accessory used in setting up the guidance device.

Figure 1:
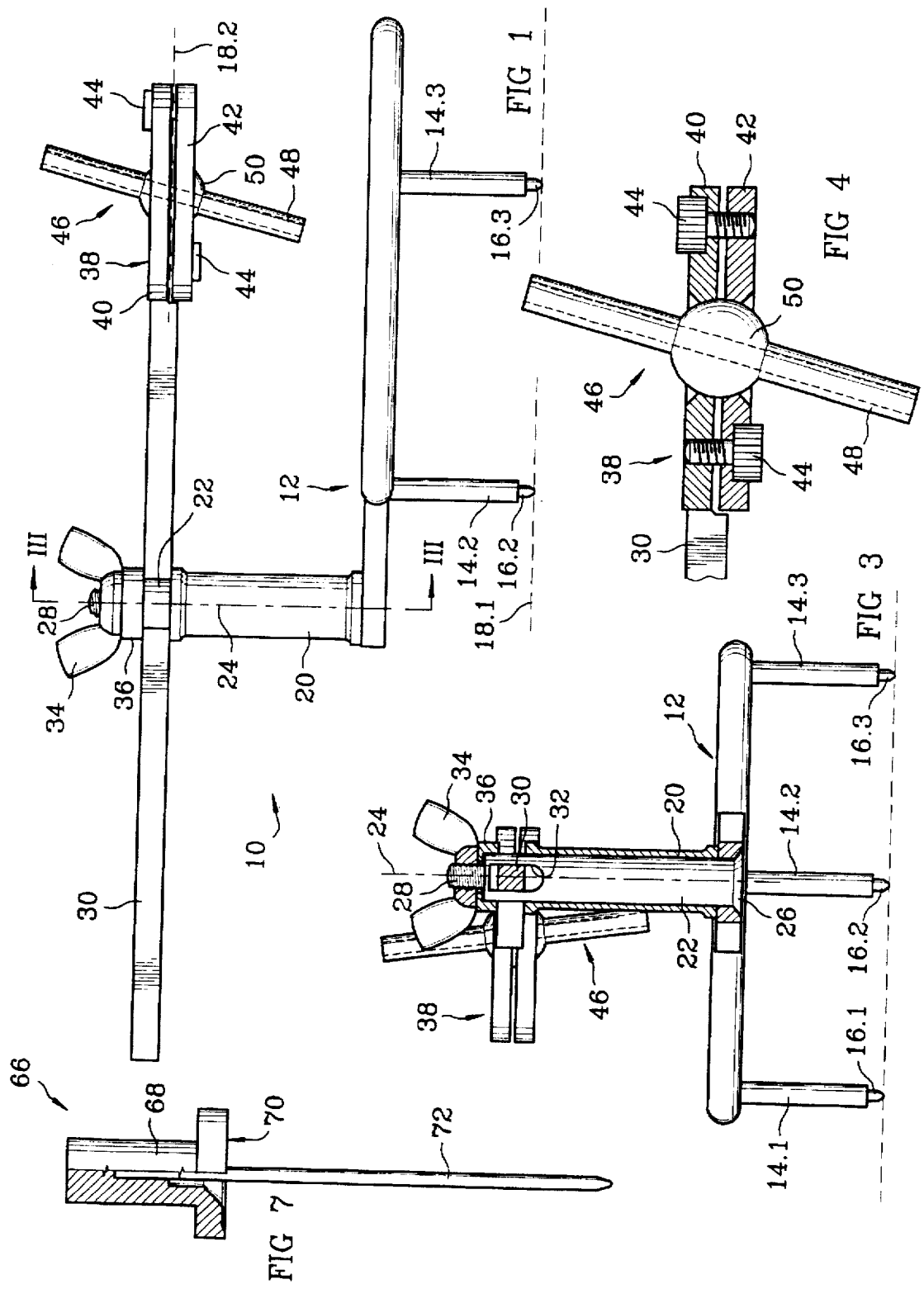
FIG. 1 is a side view of a surgical guidance device in accordance with the invention.
Figure 2:
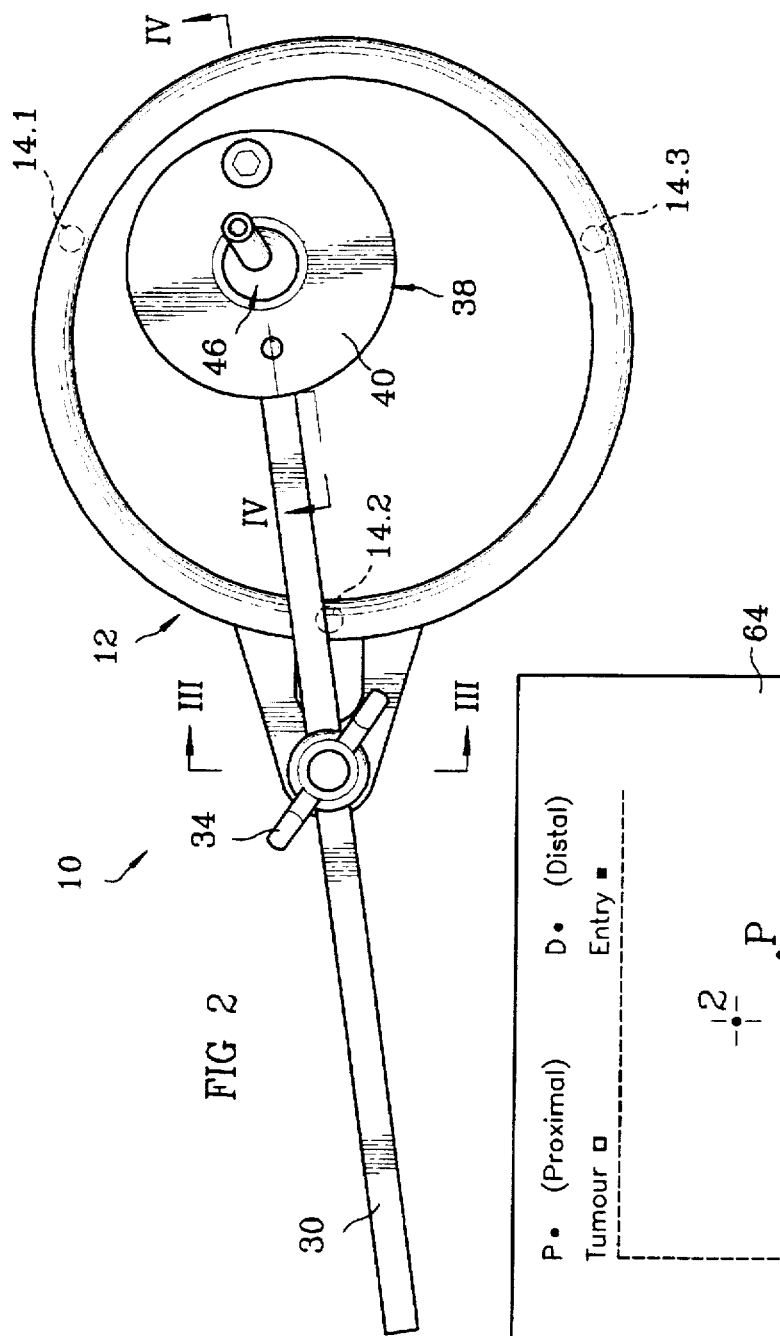
FIG. 2 is a plan view of the device.

Referring first to FIGS. 1 to 4, reference numeral 10 generally indicates a surgical guidance device comprising a base 12. The base 12 has three legs 14.1, 14.2, and 14.3, each with a pointed (but not sharp) foot 16.1, 16.2, and 16.3 respectively. The tips of the feet 16.1 to 16.3 define a first plane 18.1.

Fast with the base 12 there is an upright post 20. The post 20 is bored to receive a spindle 22 which is rotatable with respect to the base 12 about a pivot axis 24, the pivot axis being normal to the plane 18.1. The spindle 22 has a tapered head 26 at the lower end thereof, and a threaded portion 28 at the upper end thereof.

The device 10 further comprises a radius arm 30 which is of square cross-section and is slidable in a slotted opening 32 in the spindle 22. A wing nut 34 engages with the threaded portion 2B, and between the wing nut and the radius arm 30 there is a spacer ring 36. When the wing nut 34 is slightly loose, the radius arm 30 can slide along the slotted opening 32, in the longitudinal direction of the radius arm, and can pivot with respect to the base 12 about the pivot axis 24. When the wing nut 34 is tightened, the radius arm 30 is clamped between the upper face of the post 20 and the spacer ring 36. This is effective to lock the radius arm in position, locating it against sliding movement in its longitudinal direction and against pivotal movement about the pivot axis 24.

At one end of the radius arm 30 there is a swivel head 38. The swivel head 38 comprises two annular clamping plates, namely an upper plate 40 and a lower plate 42, which can be clamped together by means of a pair of clamping screws 44. The swivel head 36 carries a guide 46 which consists of a guide tube 46 having, between the ends thereof, a spherical formation 50 on the outside thereof. The clamping plates 40 and 42, in conjunction with the spherical formation 50, form a ball-and-socket connection between the swivel head 38 and the guide 46. When the clamping screws 44 are slightly loose, the guide 46 is able to pivot in all directions about a pivot point which coincides with the centre of the spherical formation 50.

The entire device is of stainless steel so that it can readily be sterilized.

The manner in which the device 10 is used, for example, to carry out a biopsy procedure on the brain of a patient will now be described, with reference also to FIGS. 5 to 8. To carry out this procedure it is necessary to bring the tip of a biopsy needle precisely to a predetermined position in the brain of the patient. The guidance device 10 has been designed to assist the surgeon in achieving this. Many of the steps described below are carried out by assistants outside the operating theatre, so that they do not take up the surgeon's time.

First, a computed tomography (ACT) scan is taken of the patient's head. Before taking the CT scan, four adhesive marker discs are placed in position on the patient's head (see FIG. 5). The first one, indicated by reference numeral 60, marks the entry point where the surgeon wishes to enter the patient's cranium. The other three marker discs, indicated by reference numerals 62.1, 62.2, and 62.3, are placed around the marker disc 60, the spacing between the centres of the marker discs 62.1, 62.2, and 62.3 corresponding to the spacing between the feet 16.1, 16.2, and 16.3 respectively. To facilitate the correct positioning of the discs 62.1 to 62.3, a template comprising three legs whose configuration is identical to that of the legs 14.1 to 14.3 may be used. Each of the marker discs 60 and 62.1 to 62.3 has a 2 mm opening at the centre thereof. After the marker discs have been placed in position, a 2 mm steel ball is placed in each of the 2 mm openings, whereupon the CT scan can commence. The steel balls form radio-opaque markers which are readily visible on the CT scan images.

The images obtained by the CT scan enable the rectangular co-ordinates (x, y, and z) of any feature shown by the CT scan to be determined. The x and y coordinates are determined by moving a cursor on the display screen when displaying a particular CT slice, to the feature in question. The z co-ordinate corresponds to the "table position" of the slice.

A conventional CT scan of the region of interest and consisting of a series of slices is taken, so as to enable the co-ordinates of the point in the patient's brain (ie the target) from where the biopsy is to be taken to be determined. The table on which the patient is supported in the CT scan apparatus is then moved to align one of the steel balls with the plane of the CT scan apparatus and a scan taken in that particular table position. This enables the coordinates of the steel ball to be determined. The process is repeated for each of the other steel balls, and then once more for the first ball to verify that no significant movement of the patient's head has taken place between the readings. Once the CT scans have been completed the steel balls can be removed.

The co-ordinates of five positions will then be available, ie those of the target, the entry point (corresponding to the centre of the marker disc 60), and the centres of each of the marker discs 62.1, 62.2, and 62.3. With these co-ordinates the guidance device 10 can be set up to guide the biopsy needle precisely to the target.

There are various ways in which the guidance device 10 can be set up. One of these, making use of a suitably programmed PC or lap-top computer linked to a printer, will now be described.

Figure 6:
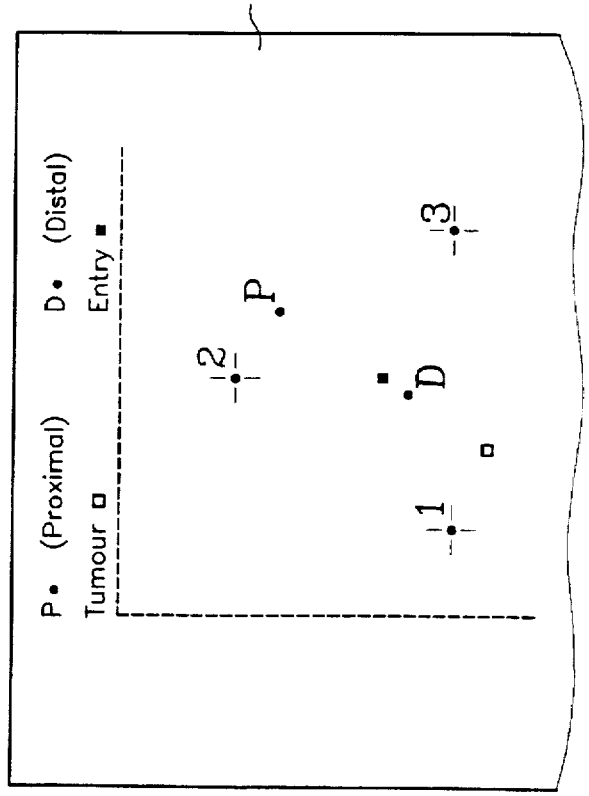
FIG. 6 illustrates a setting diagram that is produced by a PC-driven printer, for use in setting up the guidance device.

The co-ordinates of each of the various positions are entered into the computer. The computer, making use of the mathematics of three-dimensional transformations and co-ordinate geometry, computes from this data the co-ordinates, in the plane defined by the centres of the marker discs 62.1 to 62.3, of the perpendicular projections on this plane, of the entry point, the target, and the points at which a straight line passing through the entry point and the target position (the entry-point-to-target line) intersects the second plane 18.2. These computed positions, as also the positions of the centres of the marker discs 62.1 to 62.3 and the point at which the entry-point-to-target line intersects the plane 18.1, are then plotted by means of the printer on a sheet of paper, to form a setting diagram 64 as illustrated in FIG. 6. In the setting diagram the positions of the centres of the marker discs 62.1 to 62.3 are indicated by the numbers 1, 2, and 3 respectively. The point at which the entry-point-to-target line intersects the plane 18.2 is indicated by the letter P, and the point at which the entry point to target line intersects the plane 18.1 by the letter D. The setting diagram also indicates the projected positions of the entry point and the target (or tumour), as indicated in the drawing.

The setting diagram is placed on a flat supporting surface and the guidance device 10 is placed on the diagram, with the feet 16.1, 16.2, and 16.3 being in register with the points 1, 2, and 3 respectively. The triangle defined by the feet 16.1, 16.2, and 16.3 is preferably one that is not equilateral, so that only one correct position of the guidance device 10 on the plot is possible. The wing nut 34 and at least one of the clamping screws 44 are slightly loosened. This will enable the swivel head 38 to be moved to any desired position in the plane 18.2, and will also enable the guide 46 to be swivelled in any desired angular position with respect to the swivel head. The guide 46 is aligned with respect to the swivel head 38.5 so that the centre line of the guide tube 48 is normal to the planes 18.1 and 18.2. To facilitate this, an accessory 66 as illustrated in FIG. 7 is provided. The accessory 66 comprises a head 68 whose lower end defines a plane 70, and a pin 72 which extends at right angles to the plane 70. The distance between the tip of the pin 72 and the plane 70 corresponds to the distance between the upper face of the clamping plate 40 and the plane 18.1 when the centre line of the guide tube 48 is normal to the plane 18.1. The pin 72 is receivable with little clearance in the guide tube 48. The pin 72 is inserted into the guide tube 48 and manoeuvred until the plane 70 lies flat against the upper face of the clamping plate 40. When this is the case the centre line of the guide tube 48 is normal to the plane 18.1 and the tip of the pin 72 will touch or almost touch the setting diagram 64. With the wing nut 34 still in a slightly loose condition, the swivel head 38 is moved in the plane 18.2 until the tip of the pin 72 is in register with the point P on the setting diagram. The wing nut 34 is now tightened, thereby locking the swivel head 38 in position in the plane 18.2.

The accessory 66 is then removed and a longer pin (not illustrated) inserted into the guide tube 48 until its tip touches the setting diagram. The pin is now manoeuvred, thereby swivelling the guide 46, until the tip of the pin is in register with the point D on the setting diagram. The clamping screws 44 are then tightened, thereby locking the guide 46 in position with respect to the swivel head 38.

From the co-ordinates obtained in the CT scan it is also possible to determine the distance between the upper end of the guide tube 48 and the target.

This distance can be computed by the computer and printed on the setting diagram 64.

The guidance device 10 is now ready for use by the surgeon and is sterilized before going into the operating theatre.

Figure 8:
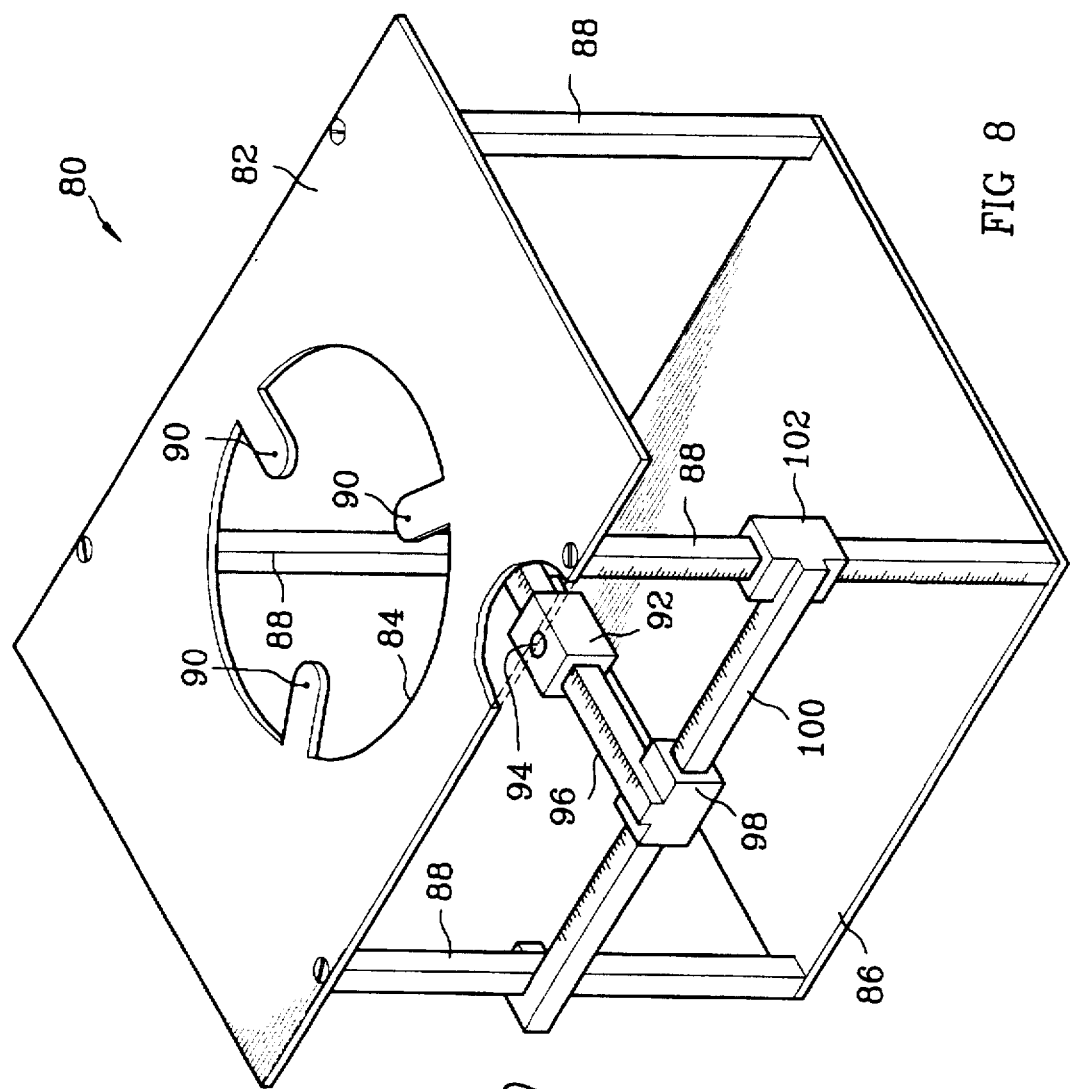
FIG. 8 is a cut-away pictorial view of a phantom used to verify the setting of the guidance device.
Figure 5:
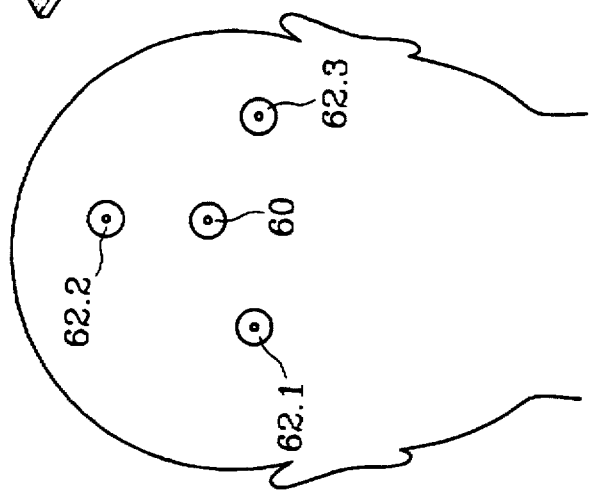
FIG. 5 shows the back of a patient's head, to illustrate one of the procedures in which the guidance device can be used.

If desired, the setting of the guidance device 10 can be verified by making use of a phantom such as the one designated 80 in FIG. 8. The phantom 80 comprises a flat plate 82 which has an opening 84 therein and is supported on a bottom plate 86 via legs 88. Spaced around the opening 84 there are three small pits 90 in parts of the plate 82 that project into the opening 84, for locating the feet 16.1 to 16.3 of the guidance device 10. The phantom 80 further comprises a block 92 with a mark 94 thereon, the mark 94 representing the target. The block 92 is slidable along a bar 96. The bar 96 is fixed to a block 98 which is in turn slidable along a bar 100, and the bar 100 is fixed to a block 102 which is in turn slidable along one of the legs 88. The bars 96 and 100, and the leg 98 in question are at right angles to one another and are each marked with graduations. The blocks 92, 98, and 102 are also each provided with a clamping screw (not shown) whereby they can be locked into any desired position along the corresponding bar or leg. This enables the target block 92 to be adjusted to a position in which the co-ordinates of the target 94 relative to the positions of the pits 90 correspond to those of the target in the patient's brain relative to the centres of the marker discs 62.1 to 62.3.

To verify the setting of the guidance device 10, a long pin (not shown) with a displaceable collar thereon is set up so that the distance between the tip of the pin and the collar corresponds to the computed distance from the upper end of the guide tube 48 to the target. The guidance device 10 is placed on the phantom 80, with each of the feet 16.1 to 16.3 seating in the corresponding pit 90, and the long pin with the collar thereon is inserted into the guide tube 48 until the collar abuts on the upper end of the guide tube. The tip of the pin should now be in register with the target 94. In this manner the surgeon will be able to satisfy himself that the setting of the guidance device is correct.

The phantom 80 can be of stainless steel construction, so that it can be sterilized for use in the operating theatre.

When the patient is ready for the surgical part of the biopsy procedure to commence, the surgeon will mark the positions of the marker discs 62.1 to 62.3 on the patient's skin with an indelible marking fluid. This can be done through the openings left by the removal of the steel balls referred to earlier. The marker discs are then removed. If desired, stainless steel marker pins having pits therein for locating the feet of the guidance device 10 may be placed on each of the marks and secured in position by driving them into the bone of the patients skull, so as to fix them with respect to the skull.

The surgeon now enters the patient's cranium at the mark that marks the entry point. Once the patient's cranium has been entered, a biopsy needle is inserted through the guide tube 48 into the patient's brain. The biopsy needle is provided with an adjustable collar which is clamped in position at a point corresponding to the distance to which it is to be inserted to reach the target. Thus, when the collar abuts on the upper end of the guide tube 48, the surgeon will know that the tip of needle is at the position of the target, whereupon a biopsy can be taken and the biopsy needle withdrawn.

I claim:

1. A surgical guidance device for the precise positioning of a surgical object, wherein the device comprises:
    a base having three feet which define a first plane, and which are adapted for location on markers secured to a patient's body;
    a swivel head which is constrained for movement in a second plane;
    a guide for the surgical object, the guide being mounted on the swivel head so that it can swivel with respect to the swivel head in all directions about a pivot point; and
    locating means for locking the swivel head in a selected translational position in the second plane and the guide in the selected angular position with respect to the swivel head.

2. A surgical guidance device as claimed in claim 1, wherein the second plane is spaced from and parallel to the first plane and wherein the swivel head is mounted on a radius arm, the radius arm being mounted on the base so as to be pivotally displaceable with respect to the base about a pivot axis normal to the first plane, and the radius arm being slidably displaceable with respect to the base or the swivel head, whereby the radial distance between the swivel head and pivot axis can be varied.

3. A surgical guidance device as claimed in claim 1, wherein the guide comprises a guide tube along which a pin forming the surgical object or having the surgical object attached thereto, can slide with little clearance, the tube being connected to the swivel head via a ball-and-socket connection.

4. A surgical guidance device as claimed in claim 3, wherein the guide tube has a spherical formation between the ends and on the outside thereof, and wherein the swivel head comprises a pair of annular clamping plates between which the spherical formation is held, the clamping the clamping plates and the spherical formation forming said ball-and-socket connection, and locking of the guide in a selected angular position with respect to the swivel head being effected by clamping the clamping plates together to grip the spherical formation therebetween.

5. A surgical guidance device kit according to claim 1, wherein, in the surgical guidance device, the second plane is spaced from and parallel to the first plane, and the feet thereof are non-sharp.

6. A surgical guidance device kit, which comprises: a surgical guidance device for the precise positioning of a surgical object and comprising a base having three feet which define a first plane, a swivel head which is constrained for movement in a second plane, a guide for the surgical object, the guide being mounted on the swivel head so that it can swivel with respect to the swivel head in all directions about a pivot point, and locking means for locking the swivel head in a selected translational position in the second plane and the guide in a selected angular position with respect to the swivel head; and three markers securable to a patient's body and on which the feet of the surgical guidance device are respectively locatable.

7. A surgical guidance device kit according to claim 6, which includes a phantom comprising a plate having an opening therein and, spaced around the opening, three locating formations whose positions relative to one another correspond to the positions of the feet of the surgical guidance device relative to one another, and further comprising a target block below the opening, the target block being slidable in three mutually orthogonal directions along graduated slides.

8. A method of guiding a surgical object to a target position in a patient, which method comprises:
    utilizing a guidance device having a base with three feet which define a first plane, a swivel head which is constrained for movement in a second plane spaced from and parallel to the first plane, and a guide for the surgical object, the guide being mounted on the swivel head so that it can swivel with respect to the swivel head in all directions about a pivot point;
    applying at least three markers to the body of the patient, the positions of the markers relative to one another corresponding to the positions of said feet relative to one another;
    determining the coordinates of the target position and each of the markers, in a three co-ordinate system;

setting up the guidance device by adjusting the translational position of the swivel head in the second plane and adjusting the angular position of the guide with respect to the swivel head;

locking the swivel head and the guide in their adjusted positions;

placing the guidance device on the patient so that the feet are in register with the positions of said markers; and inserting the surgical object into the patient along the guide.

* * * * *

UNITED STATES PATENT AND TRADEMARK OFFICE
CERTIFICATE OF CORRECTION

PATENT NO. : 5,776,143
DATED : July 7, 1998
INVENTOR(S) :
Adams

It is certified that error appears in the above-identified patent and that said Letters Patent is hereby corrected as shown below:

Claim 1, line 11 (column 5, line 61), change "locating" to --locking--;

Claim 1, line 13 (column 5, line 63), change "the selected" to --a selected--.

Signed and Sealed this

Eighth Day of December, 1998

*Attest:*

BRUCE LEHMAN

*Attesting Officer*      Commissioner of Patents and Trademarks